(12) United States Patent
Herrmann et al.

(10) Patent No.: US 9,784,719 B2
(45) Date of Patent: Oct. 10, 2017

(54) EMPTY CRATE INSPECTION BY DETECTION OF EXCITED OSCILLATIONS

(75) Inventors: Jurgen Herrmann, Rosenheim (DE); Marius Michael Herrmann, Rosenheim (DE); Xiang Zhang, Wetter (DE)

(73) Assignee: KHS GmbH, Dortmund (DE)

( * ) Notice: Subject to any disclaimer, the term of this patent is extended or adjusted under 35 U.S.C. 154(b) by 518 days.

(21) Appl. No.: 14/350,127

(22) PCT Filed: Sep. 4, 2012

(86) PCT No.: PCT/EP2012/003680
§ 371 (c)(1),
(2), (4) Date: Apr. 7, 2014

(87) PCT Pub. No.: WO2013/050096
PCT Pub. Date: Apr. 11, 2013

(65) Prior Publication Data
US 2014/0283613 A1    Sep. 25, 2014

(30) Foreign Application Priority Data

Oct. 7, 2011    (DE) .................. 10 2011 115 105

(51) Int. Cl.
| | |
|---|---|
| *B07C 5/34* | (2006.01) |
| *G01N 29/32* | (2006.01) |
| *G01N 29/27* | (2006.01) |
| *G01N 29/04* | (2006.01) |
| *G01M 7/02* | (2006.01) |

(52) U.S. Cl.
CPC ............... *G01N 29/27* (2013.01); *B07C 5/34* (2013.01); *G01M 7/027* (2013.01); *G01N 29/045* (2013.01); *G01N 29/32* (2013.01); *G01N 2291/2695* (2013.01)

(58) Field of Classification Search
CPC ...... G01N 29/045; G01N 29/27; G01N 29/32; G01N 2291/2695; G01M 7/027; B07C 5/34
USPC ........................................... 73/649
See application file for complete search history.

(56) References Cited

U.S. PATENT DOCUMENTS

| | | | | |
|---|---|---|---|---|
| 3,923,158 A | * | 12/1975 | Fornaa ............... | B07C 5/126 209/526 |
| 5,388,707 A | * | 2/1995 | Stivison ............. | B07C 5/124 198/389 |
| 5,821,424 A | * | 10/1998 | Rodriguez ......... | G01F 23/2966 73/52 |

(Continued)

FOREIGN PATENT DOCUMENTS

| | | |
|---|---|---|
| DE | 2310869 | 9/1974 |
| DE | 7407378 | 8/1977 |

(Continued)

*Primary Examiner* — J M Saint Surin
(74) *Attorney, Agent, or Firm* — Occhiuti & Rohlicek LLP (57) ABSTRACT

An apparatus for inspecting an empty crate that is transported on a transport device includes an inspection device having a pulse generator, a processor, a sensor, and an uncoupling device. Prior to inspection, the uncoupling device uncouples the empty crate from the transport device. The pulse generator then excites vibrations in the empty crate, which the sensor receives and passes to a processor for analysis.

10 Claims, 7 Drawing Sheets

(56) References Cited

U.S. PATENT DOCUMENTS

| | | | | |
|---|---|---|---|---|
| 6,298,974 B1* | 10/2001 | Heuft | ............... | B65G 47/244 198/339.1 |
| 7,108,025 B2* | 9/2006 | Bernhard | ............... | B67C 3/244 141/144 |
| 2005/0151083 A1* | 7/2005 | Favro | ............... | G01N 3/60 250/341.6 |
| 2011/0025840 A1* | 2/2011 | Fiegler | ............... | G01N 21/9027 348/127 |
| 2011/0041611 A1* | 2/2011 | Hofer | ............... | G01H 1/003 73/579 |
| 2014/0240699 A1* | 8/2014 | Lindner | ............... | B07C 5/3408 356/240.1 |

FOREIGN PATENT DOCUMENTS

| | | | | |
|---|---|---|---|---|
| DE | 2922535 | | 2/1980 | |
| DE | 3300259 | | 8/1983 | |
| DE | 4004965 | | 8/1991 | |
| DE | 10100467 | | 7/2001 | |
| DE | 10321389 | | 12/2004 | |
| EP | 0043170 | | 1/1982 | |
| EP | 0636881 | | 2/1995 | |
| EP | 1 548 430 | | 6/2005 | |
| JP | 404240080 | * | 8/1992 | ............... B25J 9/00 |
| WO | 03/045590 | | 6/2003 | |

* cited by examiner

EMPTY CRATE INSPECTION BY DETECTION OF EXCITED OSCILLATIONS

RELATED APPLICATIONS

This application is the national stage of PCT/EP2012/003680, filed on Sep. 4, 2012, which claims the benefit of the Oct. 7, 2011 priority date of German application DE 102011115105.6, the contents of which are herein incorporated by reference.

FIELD OF INVENTION

The invention relates to an inspection device for inspection of empty crates, preferably of empty plastic crates, that can accommodate, for example, drink bottles made of any desired materials, with the empty crates being transported on a transport device. The invention also relates to an inspection method with the inspection device.

BACKGROUND

Empty plastic crates may become brittle through exposure to sunlight, thereby possibly reducing their strength. Strength may also gradually diminish after long periods of use.

Empty crates can also be damaged in other ways. It is possible, for example, for the frame of an empty crate to develop hairline cracks or other cracks and holes or other damage. This can arise as a result of improper handling by consumers. Objects such as, for example, caps may also be left behind in the actual empty crate.

If a faulty crate were to be loaded with filled containers or bottles at the bottling plant, for example, and if the crate were to then break up, due for example to its existing weaknesses, there would be a significant production outage. A plant would come to a complete standstill and could only be returned to operation once the damage is rectified. For these and other reasons, empty crates should undergo an inspection before being filled with filled bottles or containers.

It is also possible for a crate to break while being handled by a consumer. In that case, the containers in the crate might then break on the floor, spilling product, including sugary drinks, on the floor. This involves extensive cleaning measures. It also adversely affects the reputation of the drink manufacturer, since consumers will most likely not bother to identify the crate manufacturer.

An inspection device can distinguish defect-free empty crates from faulty empty crates, and separate the faulty empty crates.

DE 33 00 259 discloses such a device for separating out damaged plastic crates using an ultrasound hardness tester with a vibration rod and a test probe at its head end. A drive device actuates the vibration rod in such a way that, in its pushed-in state, the test probe is in constant contact with the crate. A detector records the vibration rod's resonance frequency, which varies in the crate. Depending on the recorded resonance frequency, one can determined whether the crate is faulty or fault-free. If the crate is faulty it can then be separated out with a segregating device.

DE 103 21 389 A1 is also concerned with the defined excitation of a test specimen and recording the natural resonance, with small parts being examined for cracks and dimensional stability in this case.

DE 40 04 965 A1 is concerned with a leak testing of caps by creating and abruptly removing a magnetic field. In response, the cap rebounds and generates oscillation and/or the electrical signals. These signals, including frequencies thereof, are then processed and evaluated.

DE 74 07 378 U describes empty bottle inspection.

WO 03/45590 A1 discloses a method for detecting impurities and/or heavy materials in a mixture of waste or scrap by measuring the sound or structure-borne noise as compared with stored reference signals.

DE 2 310 869 relates to a test method for plastic-coated bottles.

A vibrometer, which is a measuring instrument for the quantifying of mechanical vibrations, is also known. Such vibrometers measure the vibration amplitude of an object.

Typically, a vibrometers has a laser that is focused on a surface whose vibrations are to be measured. As a result of the Doppler effect, which arises from the motion of the measured surface, the frequency of laser light that is back-scattered off the measured surface is shifted in frequency. This frequency shift is evaluated in the vibrometer by way of an interferometer and output as a voltage signal or digital data stream. A scanning vibrometer allows an area-related measurement of vibrations.

Laser scanning vibrometry is a fast method for the non-contact measurement and imaging of vibrations, for example in automotive, aeronautical and mechanical engineering, in microsystems and data engineering as well as in quality and production control. The optimization of vibration and acoustic behavior (e.g. operational vibration analysis) has become an important goal of product development in many of these fields because the dynamic and acoustic properties of products are some of their essential quality attributes.

In a scanning vibrometer, a laser Doppler vibrometer is integrated in a measuring head together with a scanner-mirror unit and video camera. During the measurement, the laser is scanned point-by-point over the test object's surface to provide a large number of very high spatial resolution measurements. This sequentially measured vibration data can be used to calculate and visualize animated deflection shapes in the relevant frequency bands from frequency domain analysis. Alternatively, it can be used to show vibration activity in the time domain, for example, by generating animations showing wave propagation across structures.

In contrast to contact measuring methods, the test object is essentially unaffected by the vibration measuring process. The measurement ranges accessible with known vibrometers completely cover the entire field of technically relevant vibrations. Vibrometry can thus be used to analyze, on the one hand, movements of microstructures with vibration displacements of a few picometers at frequencies up to 30 MHz (and hence v=0.1 m/s), and on the other fast-moving processes taking place in Formula 1 engines with vibration velocities up to 30 m/s.

A 3D scanning vibrometer combines three measuring heads, each of which detects dynamic movement from a different direction in space in order to completely determine the 3D vectors of motion. In the 3D representation of the vibration data, the vibrations of the measured object can be observed spatially or individually in the x, y and z directions, while in-plane and out-of-plane vector components can also be clearly differentiated.

With the known inspection devices that excite the empty crate that is to be inspected (e.g. DE 33 00 259), it is conceivable that, as a result of the standing up of the empty crate on the transport device, significant faults can corrupt the measurement result.

SUMMARY

It is an object of the invention to provide an inspection device and an inspection method that largely eliminates sources of error such that a reliable measurement result can be achieved to distinguish between faulty and fault-free empty crates.

It must be pointed out that the features which are individually listed in the claims can be combined with one another in any desired technically meaningful manner and disclose further embodiments of the invention. The description additionally characterizes and specifies the invention in particular in conjunction with the figures.

According to the invention an inspection device includes an uncoupling device that uncouples the empty crate to be inspected from the transport device for inspection purposes.

In the context of the invention, an uncoupling of the empty crate from the transport device is a complete separation of the empty crate from the transport device such that the empty crate no longer has any direct contact with the transport device during the inspection, i.e. in its inspection position. This can be achieved in a particularly simple way when the empty crate is lifted off the transport device, with the inspection not being effected until the direct contact of the empty crate in its inspection position with the transport device is removed.

Once the inspection is ended, the empty crate is naturally placed back on the transport device. The transport device is preferably a linear transport device, such as a transport belt. The transport belt has two laterally disposed legs that, between them, create a centrally disposed clearance.

It is advisable to briefly halt the empty crate in order to inspect it. To this end, the inspection device has at least one stop element that can be moved from a rest position to a stop position and back. The stop element can be swung out by way of a pivoting device when the empty crate to be inspected enters the inspection device. The stop element is preferably arranged on either side of the transport device, it being sufficient for the stop element to project into the empty crate's trajectory just a short way to enable the empty crate to be stopped. In alternate embodiments, a single stop device is provided on just one side of the transport device. In the stop position this could extend as far as the opposite side of the transport device.

It is expedient for the stop element or elements to be arranged in such a way that the empty crate is held to the uncoupling device so that the latter can engage with the base of the empty crate with a support element. The empty crate can be lifted up from the transport device by way of lifting devices such that the empty crate rests with its base on the support element.

Once the empty crate is lifted up from the transport device, it is in its inspection position. To commence inspection, the empty crate is made to vibrate. This is carried out by a suitable device, such as a pulse generator, for example clappers. In some embodiments, the support element has the additional function of exciting the vibrations.

The inspection device has at least one sensor that is configured a vibrometer. In some embodiments, the sensor is a laser vibrometer. The sensor captures data and transmits it to a processor or evaluator. The processor or evaluator is, in turn, connected either wirelessly or by wire to a control unit.

Some embodiments have a plurality of sensors. The pulse generators or clappers can be arranged on the support element, or also each laterally and/or at the head end, i.e. opposite the base of the empty crate. In other embodiments, just a single pulse generator may also be provided on one of the sides.

The sensor or receiver is preferably be arranged above the empty crate, but this is of course not intended to be limiting.

Although the empty crate is lifted up from the transport device and a reliable inspection result can thus be expected, it can be wholly advisable to execute the support element in a particular fashion as regards vibration engineering. Preference is given to an embodiment in which a sound board alters vibrations in a defined way, i.e. for example amplifies them to a defined degree. The use of a sound board has a further positive effect on an already reliable inspection result because the sound board eliminates possible distorting factors. This ensures that during vibration analysis of the empty crate, only one component is evaluated, with other components are ignored.

It is expedient if the lifting device includes at least one or more identically-acting lifting-cylinders, each of which engages the support element from beneath, i.e. opposite the base of the empty crate. The lifting device can be actuated for example by the aforementioned control unit, which controls not only the transport device and inspection device but upstream and downstream apparatus as well. Such a control unit is fundamentally known and so will not be described any further here. A separate standalone control device may also be provided.

When the inspection device detects a faulty empty crate, for example a crate having hairline cracks, cracks and/or holes, or one that conceals objects, such as caps, the evaluator generates a signal for separating out the faulty empty crates. This signal is passed to the control unit, which then sends a corresponding control signal to the separating device. The separating device can be configured as a crate-pusher that conveys the faulty crate onto a discharge track.

If the detected fault can be rectified, empty crates that have been separated out may be returned to the stream of empty crates. It may for example be possible to remove objects. If this is the case, the affected empty crate is loaded upstream of the inspection device and re-inspected.

The invention expediently provides for the empty crate that is to be inspected to be separated from the transport device for inspection. The inspection itself is performed by vibrating the empty crate, capturing the vibrations, and evaluating them.

The act of lifting up from the transport device ensures that harmful influences of other components can be eliminated, and this is further positively influenced by a particular embodiment of the support element. The measurement results therefore permit reliable statements regarding whether or not an empty crate should be segregated or remain.

BRIEF DESCRIPTION OF THE DRAWINGS

Further advantageous embodiments of the invention are disclosed in the dependent claims and the following description of the Figures, in which:

In the different figures, identical parts are identified by the same reference character.

DETAILED DESCRIPTION

Figure 1:
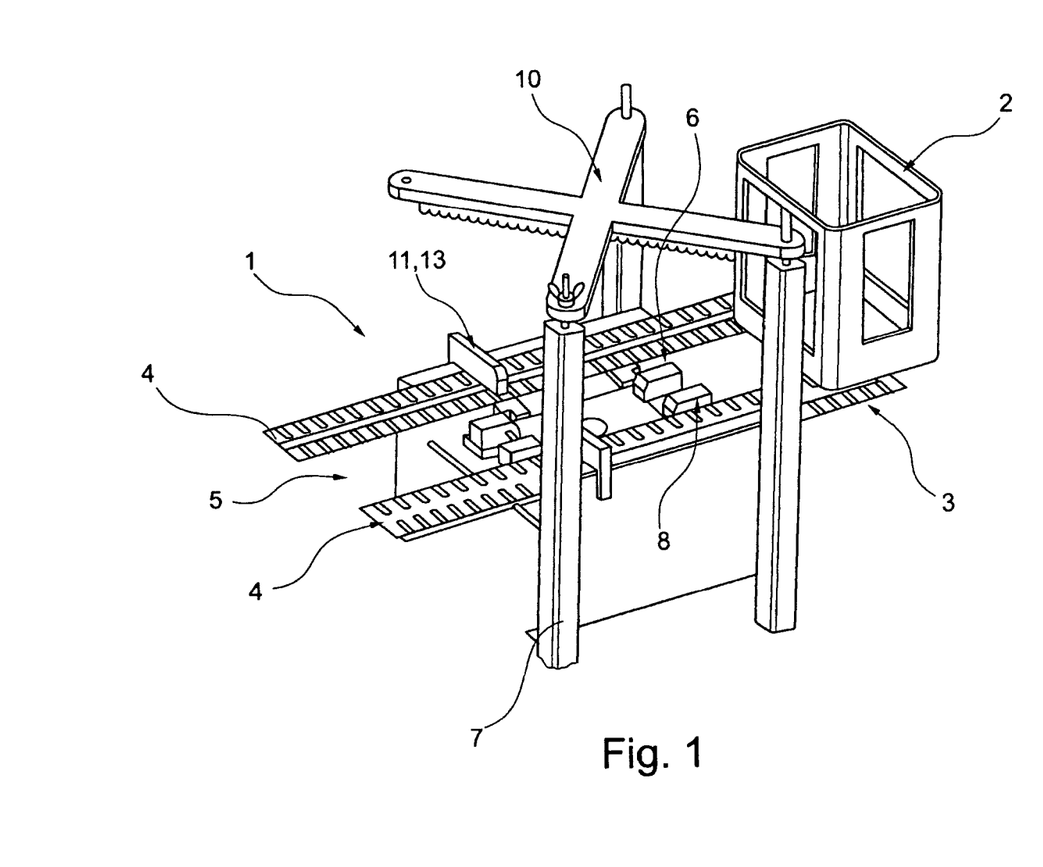
FIG. 1 shows a schematic view of an inspection device

FIG. 1 shows an inspection device 1 for the inspecting of empty crates 2 in which for example drink bottles of any desired materials may be received. The empty crates 2 are transported on a transport device 3. Preferably, the empty crates 2 are plastic empty crates.

The illustrated transport device 3 is of linear design and has two laterally disposed conveyor belts 4 separated from one another by a central clearance 5.

An uncoupling device 6 is disposed in clearance 5. The uncoupling device 6 uncouples an empty crate 2 that is to be inspected from transport device 3. In one embodiment, it does so by lifting the empty crate.

Figure 2:
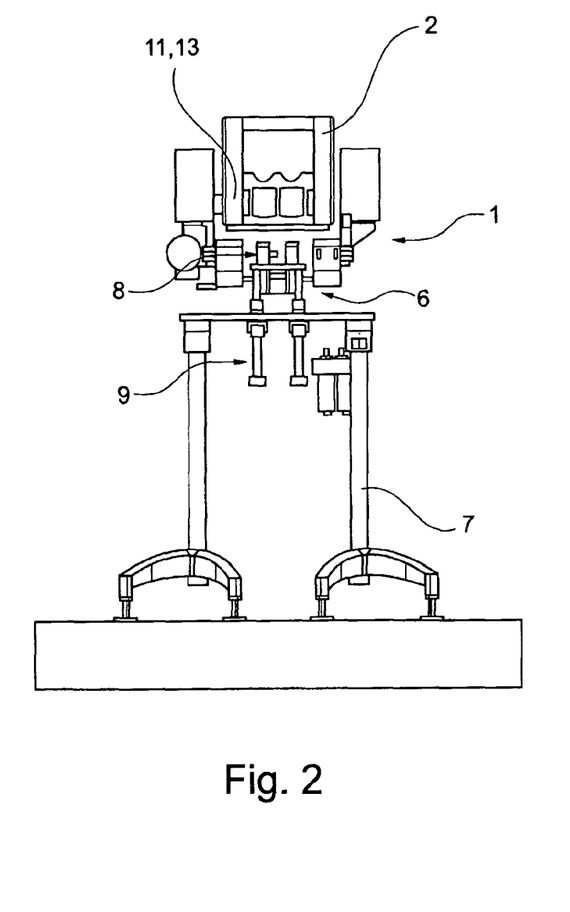
FIG. 2 shows a schematic representation of the uncoupling device.

In the particular example shown in FIGS. 1 and 2, the inspection device 1 and the uncoupling device 6 are arranged on an open frame 7. In other embodiments, inspection device 1 together with uncoupling device 6 may also be partially or wholly enclosed.

The uncoupling device 6 has a support element 8 and lifting devices 9 that engage with support element 8 from the latter's underside. In the particular embodiment shown, the lifting devices 9 are lifting cylinders. The lifting devices 9 are connected to a control unit (not shown).

The uncoupling device 6 is advantageously adapted to clearance 5 such that the uncoupling device 6 extends across the clearance with its support element(s) 8 in the raised position so that an empty crate 2 is lifted up from transport device 3.

The inspection device 1 includes elements that excite vibrations in the empty crate 2. The vibrations are captured and evaluated by a sensor or receiver 10. The receiver 10 can be a vibrometer disposed above the empty crate 2. The elements for the excitation of the empty crate 2 can comprise pulse generators, for example clappers, and arranged on the support element 8, or also laterally and/or at the head end, i.e. opposite the base of the empty crate 2.

The inspection device 1 and/or uncoupling device 6 includes stop elements 11 that can be transferred from a rest position 12 (FIG. 6) into a stop position 13 and back. When in their stop position 13, the stop elements 11 each project laterally into the transport path of the transport device 3. When in their rest position 12, the stop elements 11 are swung out of the transport path. The mechanisms for the transition between the rest position 12 and the stop position 13 are conventional enough to not require further description.

A faulty empty crate can be distinguished from a fault-free empty crate by the inspection. If a faulty empty crate is detected, a corresponding signal is generated for separating out the affected empty crate. At a separating device, a crate-pusher conveys the affected empty crate onto a discharge track.

FIGS. 3 to 7 schematically show the individual steps of the empty crate inspection.

Figure 3:
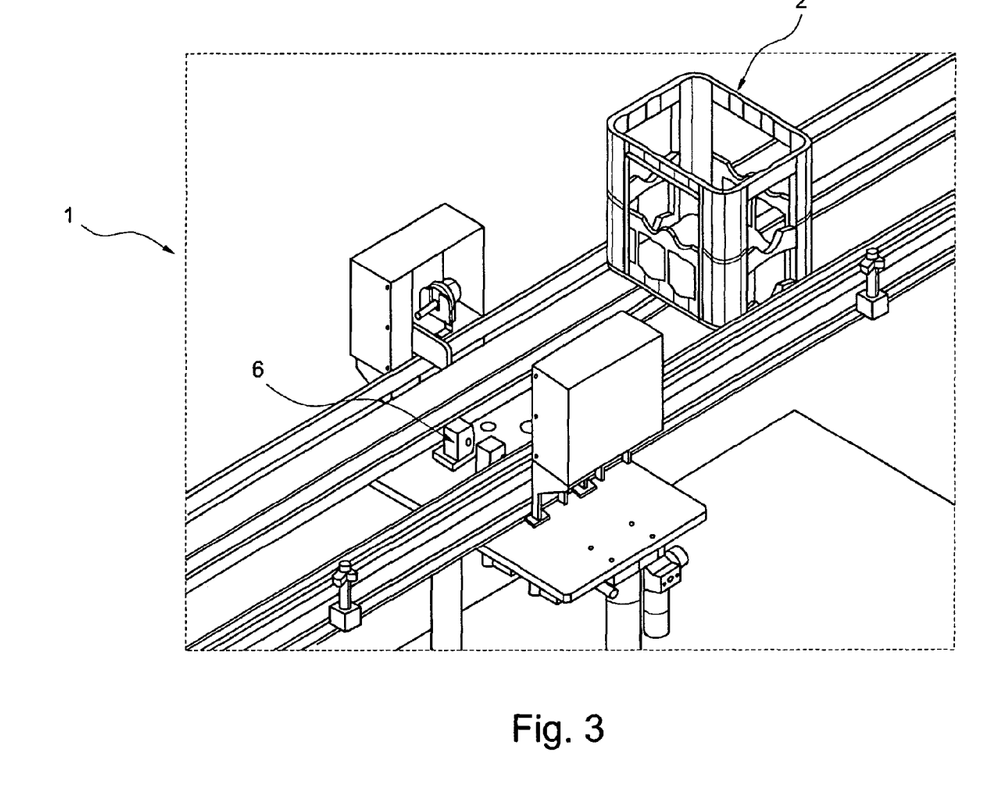
FIGS. 3-7 shows the individual steps from the entry of the empty crate to its exit from the inspection device.

In FIG. 3, the empty crate 2 is conveyed on transport device 3 towards inspection device 1.

Figure 4:
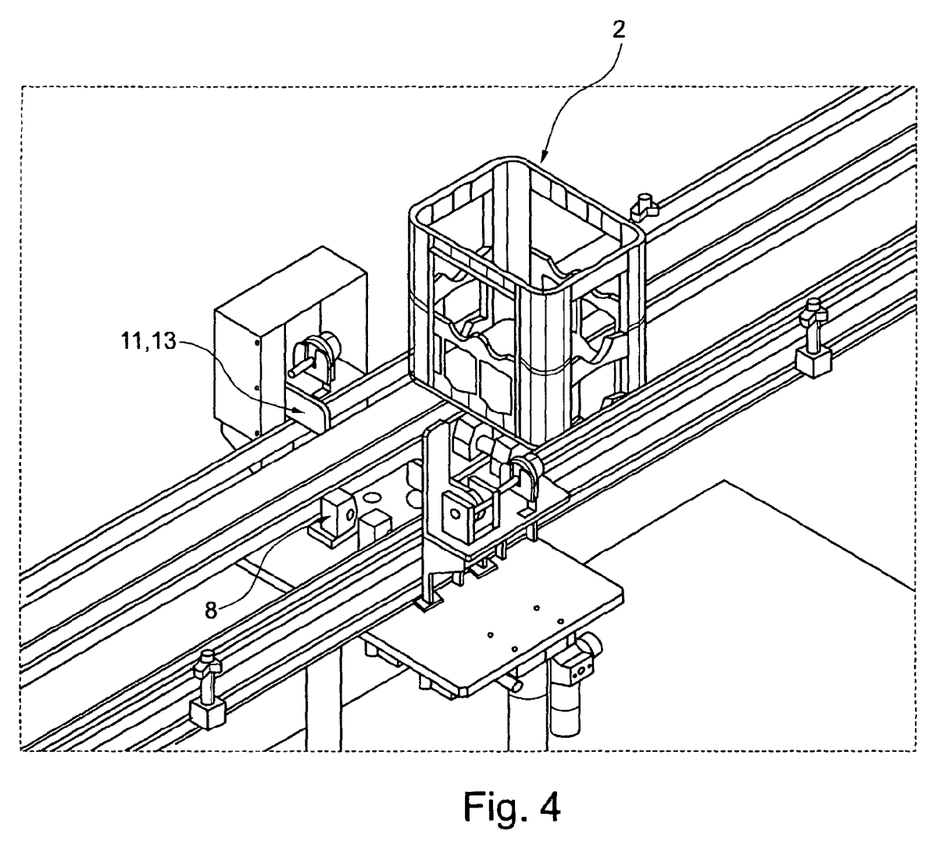

In FIG. 4, the empty crate 2 reaches an inlet position on the transport device 3 as detected by the control unit by way of corresponding signals. The control unit generates a signal to extend the stop elements 11 out of their rest position 12 and into their stop position 13.

Figure 5:
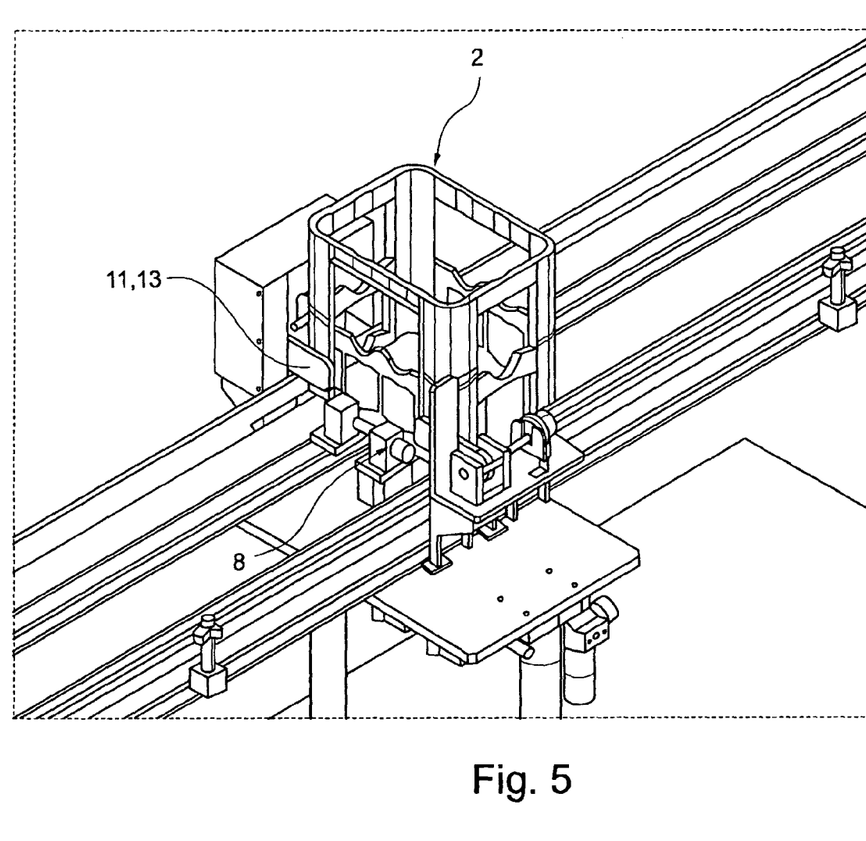

In FIG. 5, The empty crate 2 is held by stop elements 11 in the inspection position in which the empty crate 2 is completely separated and/or lifted up from the transport device 3 by the uncoupling device 6. The empty crate 2 stands on the support element 8.

In the inspection position, vibrations are excited in empty crate 2 and evaluated by the receiver 10. This results in generation of a corresponding signal for distinguishing between a faulty or fault-free empty crate 2.

The empty crate advantageously remains in inspection position 1 for a relatively short period of time so that an inspection capacity of, for example, 3,000 empty crates per hour is achievable. More or fewer empty crates can be inspected.

It is especially expedient that the empty crate 2 be separated, i.e. is lifted up from, the transport device 3 when in the inspection position. This may be detrimental to the attainable inspection capacity, as the empty crate is stopped. But this disadvantage is more than outweighed by the especially reliable inspection result.

Figure 6:
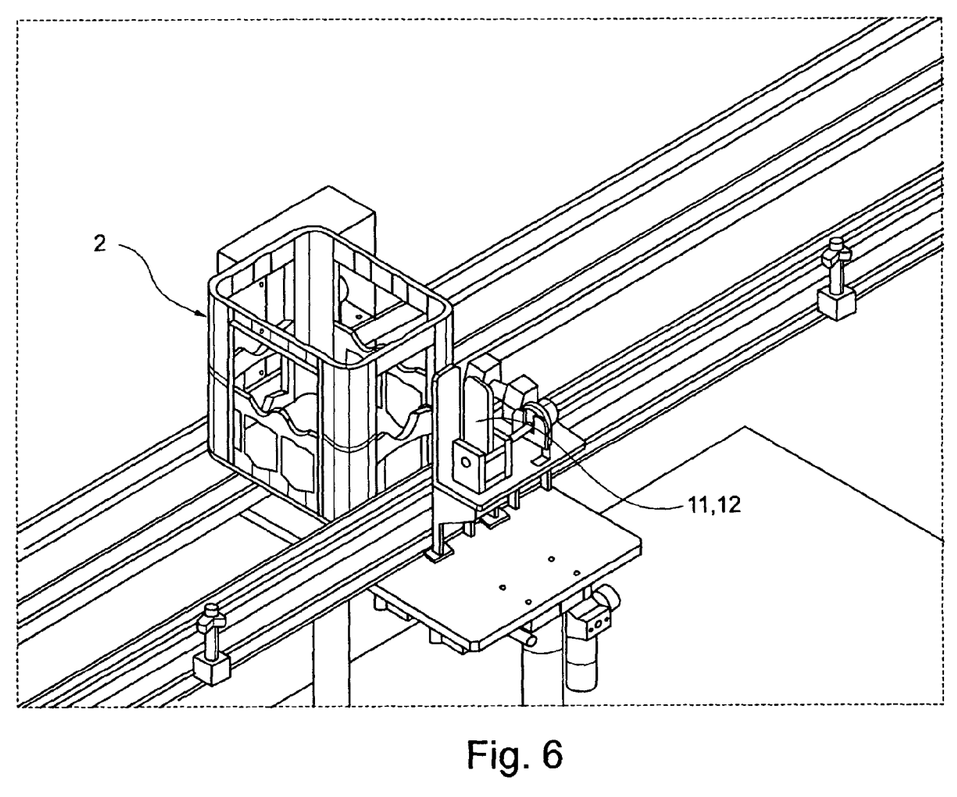
Figure 7:
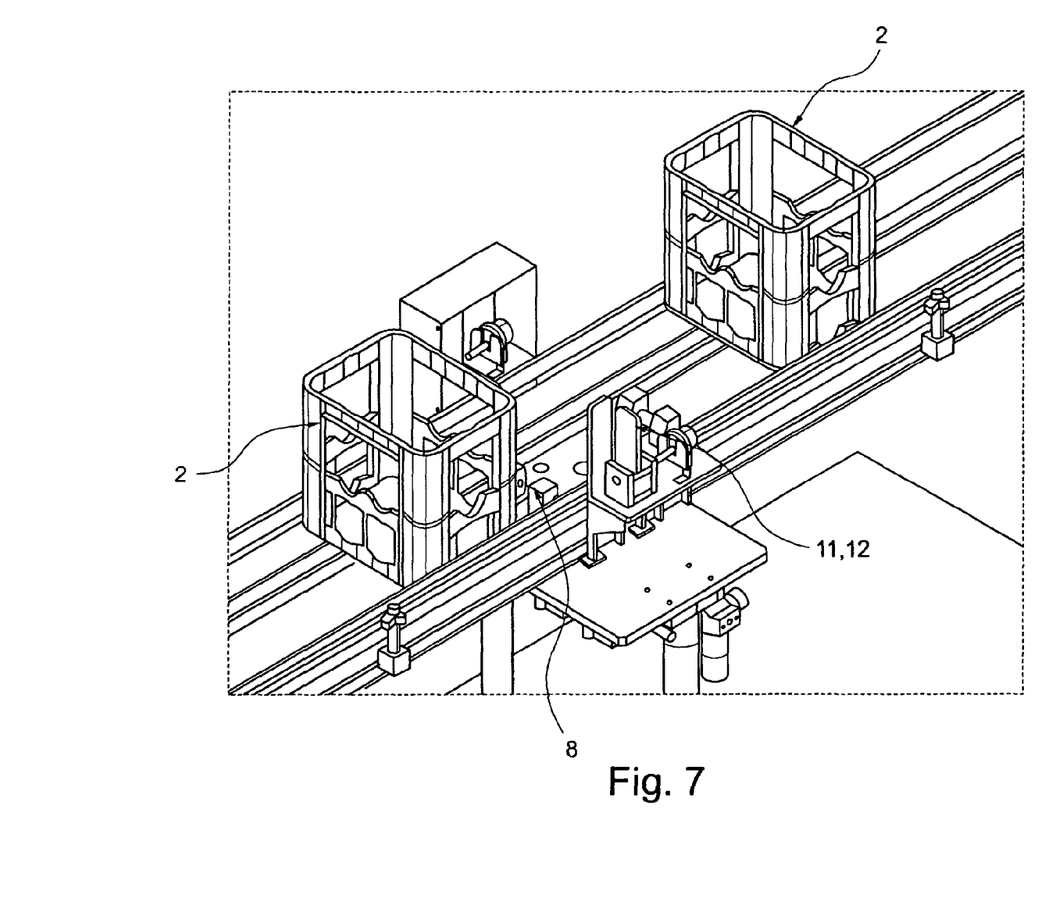

Once the inspection has ended, empty crate 2 is set down on the transport device 3 by way of the lifting device 8, the stop elements 11 having first been swung and/or rotated into rest position 12, as shown in FIG. 6. The empty crate 2 is thus transported out of inspection device 1. FIG. 7 depicts how a further empty crate 2 is transported to the inspection device 1.

To facilitate understanding of the invention, the reference numerals used for the various parts described in the figures are summarized in the table below:

1 Inspection device
2 Empty crate
3 Transport device
4 Conveyor belts of 3
5 Clearance between 4
6 Uncoupling device
7 Frame
8 Support element
9 Lifting device
10 Sensor/receiver
11 Stop elements
12 Rest position
13 Stop position Having described the invention, and a preferred embodiment thereof, what is claimed as new and secured by letters patent is:

1. An apparatus for inspecting empty crates that are transported on a transport device, said apparatus comprising an inspection device, said inspection device comprising a pulse generator, a processor, a sensor, and an uncoupling device, wherein said pulse generator is configured to excite vibrations in an empty crate from said empty crates, wherein said sensor is configured for receiving said vibrations, wherein said sensor is coupled to said processor, and wherein said uncoupling device is configured to uncouple said empty crate from said transport device for inspection of said empty crate.

2. The apparatus of claim 1, wherein said pulse generator comprises a clapper, and wherein said sensor comprises a vibrometer.

3. The apparatus of claim 1, further comprising a stop element, wherein said stop element is movable between a rest position and a stop position.

4. The apparatus of claim 1, wherein said uncoupling device further comprises a support element, and wherein, during inspection thereof, said empty crate stands on said support element.

5. The apparatus of claim 4, wherein said uncoupling device and said support element are disposed in a clearance between conveyor belts of said transport device.

6. The apparatus of claim 1, wherein said uncoupling element comprises a lifting device, wherein said lifting device lifts said empty crate into an inspection position.

7. The apparatus of claim 6, wherein said sensor comprises a laser vibrometer.

8. A method for inspecting an empty crate that is transported on a transport device, said method comprising transferring said empty crate to an inspection position, and inspecting said empty crate only when said empty crate is in said inspection position.

9. The method of claim 8, wherein inspecting said empty crate comprises causing said empty crate to vibrate, recording data representative of said vibrations, and analyzing said data.

10. the method of claim 9, wherein recording data representative of said vibrations comprises using a vibrometer, and wherein causing said empty crate to vibrate includes using a clapper to cause said vibrations.

* * * * *